United States Patent [19]

Bastos et al.

[11] Patent Number: 5,708,022
[45] Date of Patent: Jan. 13, 1998

[54] METHOD FOR INHIBITING IMMUNE RESPONSE

[75] Inventors: Cecilia M. Bastos, Marlborough; Timothy D. Ocain, Framingham, both of Mass.

[73] Assignee: Procept, Inc., Cambridge, Mass.

[21] Appl. No.: 482,308

[22] Filed: Jun. 7, 1995

Related U.S. Application Data

[63] Continuation-in-part of Ser. No. 331,204, Oct. 28, 1994, abandoned.

[51] Int. Cl.$^6$ .................................................. A61K 31/28
[52] U.S. Cl. ................................................... 514/492
[58] Field of Search ................................ 514/188, 184, 514/187, 492

[56] References Cited

U.S. PATENT DOCUMENTS

| | | | |
|---|---|---|---|
| 4,843,069 | 6/1989 | Keller et al. | 514/184 |
| 5,238,689 | 8/1993 | Dwyer et al. | 424/617 |

FOREIGN PATENT DOCUMENTS

| | | |
|---|---|---|
| WO86/00804 | 2/1986 | WIPO. |
| WO86/04358 | 7/1986 | WIPO. |
| WO86/00905 | 2/1996 | WIPO. |

OTHER PUBLICATIONS

Bora et al., "Compounds of Imidazoles with Ruthenium (III) Chloride", *Transition Met. Chem.* 11:467–469 (1986).

Sundberg et al., "Nitrogen–Bound and Carbon–Bound Imidazole Complexes of Ruthenium Ammines", *J. Amer. Chem. Soc.*, 96(2):381–92 (1974).

Sudha et al., "Electrochemical Evidence for a Two–Electron Reduction Process in a (μ–Oxo)bis(μ–acetato) diruthenium (III) Complex Containing Terminal 1–Methylimidazole Ligands", *Inorganic Chem.*, 32:3801–3802 (1993).

Heijden et al., "Synthesis and Characterization of cis–(2, 2'–Bipyridine)(2,2'–biquinoline)dichlororuthenium (II) and its Co–ordination Chemistry with Imidazole Derivatives", *J. Chem. Soc. Dalton Trans.*, 24:3675–9 (1993).

Krusyna et al., "Toxicology and Pharmacology of Some Ruthenium Compounds: Vascular Smooth Muscle Relaxation by Nitrosyl Derivatives of Ruthenium and Iridium", *J. Toxicol. Environ. Health*, 6:757–773 (1980).

Grover et al., "Ruthenium Red Improves Postischemic Contractile Function in Isolated Rat Hearts", *J. Cardiovasc. Pharmacol.*, 16(5):783–9 (1990).

Tanaka et al., "Inhibitors of Calcium–Dependent Cyclic Nucleotide Phosphodiesterase", *Chemical Abstracts*, 117(26): 25823, p. 457 (1992).

Tomiyama et al., "Beta–Adrenergic Blocking Action of Ruthenium Red", *Japan J. Pharmacol.*, 23(6):889–91, (1973).

Anghileri, L., "The in vivo Inhibition of Tumor Growth by Ruthenium Red: Its Relationship with the Metabolism of Calcium in the Tumor", *Z. Krebsforsch*, 83:213–217 (1975).

Keppler et al., "Synthesis, Molecular Structure, and Tumor––Inhibiting Properties of Imidazolium trans–Bis(imidazole )tetrachlororuthenate(III) and Its Methyl–Substituted Derivatives", *Inorg. Chem.*, 26(26):4366–4370 (1987).

*Primary Examiner*—Theodore J. Criares
*Attorney, Agent, or Firm*—Hamilton, Brook, Smith & Reynolds, P.C.

[57] ABSTRACT

Use of ruthenium complexes as immunosuppressive agents to prevent or significantly reduce graft rejection in organ and bone marrow transplantation is described. The ruthenium complexes can also be used as immunosuppressant drugs for T-lymphocyte mediated autoimmune diseases, such as diabetes, and may be useful in alleviating psoriasis and contact dermatitis. The ruthenium complexes can also be used therapeutically in the treatment of hyperproliferative vascular disease.

28 Claims, No Drawings

1

METHOD FOR INHIBITING IMMUNE RESPONSE

RELATED APPLICATION

This is a Continuation-in-Part application of U.S. Ser. No. 08/331,204, filed Oct. 28, 1994, now abandoned, the entire teachings of which are incorporated herein by reference.

BACKGROUND OF THE INVENTION

Replacement of defective or severely injured tissues and organs has been a medical objective as long as medicine has been practiced. Grafts from an individual to himself almost invariably succeed, and are especially important in the treatment of burn patients. Likewise, grafts between two genetically identical individuals almost invariably succeed. However, grafts between two genetically dissimilar individuals would not succeed without immunosuppressive drug therapies. The major reason for their failure is a T cell mediated immune response to cell-surface antigens that distinguish donor from host.

Immunosuppressive agents are also indicated in the treatment of autoimmune diseases such as rheumatoid arthritis or type I diabetes mellitus. One particular condition worth mentioning here is psoriasis. This disease is characterized by erythematous patches of skin accompanied by discomfort and itching. Hyperplasia of the epidermis involving proliferation of keratinocytes is also a hallmark feature of psoriasis. An inflammatory component is suggested by: (i) the finding of lymphocytic infiltration of epidermis, and (ii) the fact that immunosuppressive agents such as cyclosporin and corticosteroids have beneficial effect on the disease.

A number of drugs are currently being used or investigated for their immunosuppressive properties. Among these drugs, the most commonly used immunosuppressant is cyclosporin A. However, usage of cyclosporin has numerous side effects such as nephrotoxicity, hepatotoxicity and other central nervous system disorders. Thus, there is presently a need to investigate new immunosuppressive agents that are less toxic but equally as effective as those currently available.

SUMMARY OF THE INVENTION

This invention relates to the use of ruthenium complexes as immunosuppressive agents to prevent or significantly reduce graft rejection in organ and bone marrow transplantation. The ruthenium complexes can also be used as an immunosuppressant drug for T lymphocyte mediated autoimmune diseases, such as diabetes, rheumatoid arthritis, multiple sclerosis, lupus erythematosus and steroid resistant asthma.

In another aspect, other diseases with suspected inflammatory components, such as psoriasis, contact dermatitis and hyperplasia of the epidermis, can be treated with a ruthenium complex of this invention to alleviate symptoms associated with these disease states.

It has also been demonstrated that the ruthenium complexes have antiproliferative properties and in particular can inhibit cardiac smooth muscle cells. Based upon this, the ruthenium complexes can be used for the treatment of hyperproliferative vascular disorders, such as restenosis and atherosclerosis.

DETAILED DESCRIPTION OF THE INVENTION

This invention is based upon the discovery that ruthenium complexes can inhibit antigen specific T lymphocyte proliferation in vitro. The data suggest that ruthenium complexes have potential use as immunosuppressants to reduce undesirable immune responses in humans. Ruthenium complexes can be used to facilitate organ transplantation, and to treat human autoimmune disorders where the specific activation of T cells is responsible for, or contributes to the pathology and progression of the diseases, such as diabetes, rheumatoid arthritis, multiple sclerosis, lupus erythematosus and steroid resistant asthma.

This invention pertains to novel ruthenium complexes that have immunosuppressive properties of the general formula:

wherein Ru is ruthenium having an oxidation state of 2, 3 or 4;

wherein M is a monodentate ligand selected from the group consisting of nitrogen containing ligands, phosphorus containing ligands, sulfur containing ligands, oxygen containing ligands and halide;

wherein m is 0, 1, 2, 3, 4 or 6;

wherein b is 0, 1, 2 or 3;

wherein t is 0, 1 or 2;

wherein p is 0 or 1;

wherein m+b+t+p is 1, 2, 3, 4, 5 or 6;

wherein B is a bidentate ligand selected from the group consisting of aliphatic amines, heterocyclic aromatic amines, sulfur containing ligands, oxygen containing ligands and phosphorus containing ligands;

wherein T is a tridentate ligand selected from the group consisting of nitrogen containing ligands, sulfur containing ligands, oxygen containing ligands and phosphorus containing ligands;

wherein P is a polydentate ligand selected from the group consisting of nitrogen containing ligands, oxygen containing ligands, sulfur containing ligands and phosphorus containing ligands;

wherein when the complex is charged then Z is a counterion, for example a counterion of appropriate charge to render the overall charge of the complex neutral selected from the group consisting of $F^-$, $Cl^-$ $Br^-$, $I^-$, $NO_3^-$, $NH_4^+$, $NR_4^{1+}$, $PF_6^-$, $BPh_4^-$, $SO_4^{-2}$, $S_8^{-2}$, $S_2O_7^{-2}$, $RuCl_4^{-2}$, $K^+$, $Na^+$, $Li^+$, $ClO_4^-$, and $R^1ImH^+$, where Im is imidazole; and wherein $R^1$ is a linear or branched alkyl of 1 to 4 carbon atoms or aryl.

The coordination sphere of the metal center may contain all six ligands (referred to as monodentate) to be equivalent or a mixture of different ligands. The mixture of ligands can consist of different monodentate ligands; a mixture of bidentate/monodentate in a ratio of 1:4 or three bidentate ligands; a mixture of bidentate/tridentate/monodentate in a ratio of 1:1:1; two tridentate ligands; or tridentate/monodentate in a 1:3 ratio; or a mixture of polydentate and bidentate in a ratio of 1:1; or a mixture of polydentate/monodentate in a 1:1 or 1:2 ratio depending on the nature of the polydentate ligand.

For the purposes of this application, the terms "monodentate", "bidentate" and "tridentate" will have their generally accepted meaning in the art. That is, a monodentate ligand is defined as a chemical moiety or group which has one potential coordinating atom. More than one potential coordinating atom is termed a multidentate ligand where the number of potential coordinating atoms is indicated by the terms bidentate, tridentate, etc.

Ruthenium complexes of this invention can contain a ruthenium metal center of different oxidation states, e.g., Ru(II), Ru(III) or Ru(IV). The complex may also contain a counterion of appropriate charge to render the overall charge of the complex neutral. Suitable counterions for cationic complexes, include but are not limited to, halide $F^-$, $Cl^-$, $Br^-$ or $I^-$), $SO_4^{-2}$, $S_8^{-2}$, $S_2O_7^{-2}$, $PF_6^-$, $BPh_4^-$, $RuCl_4^{-2}$, $ClO_4^-$ and $NO_3^-$. Examples of suitable counterions for anionic complexes include but are not limited to $Na^+$, $K^+$, $Li^+$, $NH_4^+$, $NR_4^{1+}$ and $R^1Im^+$ where $R^1$ is a linear or branched alkyl of 1 to 4 carbons or aryl group and Im is imidazole.

In one embodiment, the ruthenium complex can comprise six monodentate ligands which can contain nitrogen (e.g., heterocyclic aromatic amines, aliphatic amines), sulfur, phosphorus or oxygen groups. Examples of suitable ligands include but are not limited to imidazole, pyridine, ammonia, triazole, picoline, pyrazole, quinoline, pyrazine, pyridazine, pyrimidine, quinoxaline, quinazoline, isoquinazoline, piperidine, phosphine, phosphite, thiolate, sulfoxide, alkoxide, phenolate and carboxylate. Derivatives of these ligands can also be incorporated into the complex in various combinations with the non-substituted ligands. A derivative is a ligand in which one or more of the hydrogen atoms has been substituted with a moiety, such as C1–C5 alkyl, C2–C4 alkenyl, hydroxy, nitro, amino, carboxyl, ester, di-C1–C4 alkyl amine, phenyl, benzyl, imidazole and combinations of these. Preferred ligands are imidazole derivatives having the general formula:

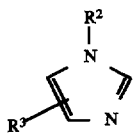

where $R^2$ and $R^3$ are independently selected from the group consisting of aryl, heteroaryl, linear and branched (e.g., 1 to 8 carbons) alkyl, —C(O)H, —COOR$^1$, —CONR$^1$, —COOH, —CH$_2$NH$_2$, —CH$_2$OSO$_2$, —CH$_2$COH, —CH$_2$COR$^1$, —CH$_2$CONR$^1$, —CH$_2$COOH, H, Cl, Br, I and NO$_2$.

Preferred ligands also include pyridine derivatives having the following general formula above:

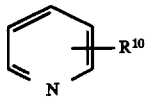

Examples of preferred ruthenium complexes having monodentate ligands are listed below.

[Ru(Im)$_6$]Cl$_2$ where Im=imidazole
[Ru(1-MeIm)$_6$]Cl$_2$ where 1-MeIm =1-methyl imidazole
[Ru(1-MeIm)$_6$](PF$_6$)$_3$
[Ru(1-MeIm)$_6$]Cl$_3$
[Ru(Im)$_6$]Cl$_3$
trans-[Ru(NH$_3$)$_4$(Im)(py)]Cl$_3$
cis-[Ru(NH$_3$)$_4$(IM)$_2$]Cl$_3$
trans-[Ru(NH$_3$)$_4$(IM)$_2$]Cl$_3$
[Ru(NH$_3$)$_5$(L-his)]Cl$_3$
[Ru(NH$_3$)$_5$(py)]Cl(RuCl$_4$)
cis-[Ru(NH$_3$)$_4$(py)$_2$]Cl$_3$
[Ru (NH$_3$)$_5$(4-pic)]Cl$_3$
cis-[Ru(NH$_3$)$_4$(1-MeIm)$_2$]Cl$_3$
[Ru(NH$_3$)$_3$(Im)$_3$]Cl$_3$ In another embodiment, a ruthenium complex can be made having multidentate ligands, in combination with other multidentate ligands and/or monodentate ligands. Suitable bidentate ligands (B) will include, but are not limited to, aliphatic amines (e.g., ethylene diamine, propylene diamine, 1,2-cyclohexane diamine and the corresponding alkylated amines thereof); heterocyclic aromatic amines (e.g., 2,2'-bipyridine, 1,10-phenanthroline); pyridine based ligands (e.g., 2-aminopicoline); pyrazole based ligands (e.g., potassium-bis-pyrazolyl borate, bis-pyrazolyl methane); carboxylates; and bis-phosphines (e.g., 1,2-bis (dimethylphosphino)ethane). Preferred are imidazole based ligands having the general formula:

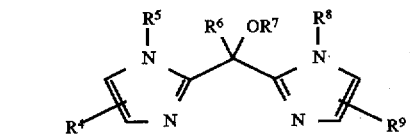

where $R^4$ to $R^9$ can be the same or different and are selected from the substituents defined above for $R^2$ to $R^3$.

The ligand can be tridentate ligand (T) such as aromatic heterocyclic amines (e.g., 2,2',6",2"-terpyridine, bis-(2-pyridylmethyl)amine); imidazole based ligands (e.g., bis-(2-imidazolylmethyl)amine); pyrazole based ligands (e.g., potassium tris pyrazolyl borate); macrocyclic amines (e.g., 1,4,7-triazacyclononane); macrocyclic sulfur based ligands (e.g., 1,4,7-trithiacyclononane and 2-(arylazophenyl)thio ether); and macrocyclic oxygen containing ligands Na{(C$_5$H$_5$)Co[P(O)R$_2$]$_3$}.

The ligand can be a polydentate ligand (P) such as nitrogen containing ligands (e.g., 1,4,7,10-tetraazacyclododecane; 1,4,8,11-tetraazacyclotetradecane; 1,3,5,7-tetrakis-(2-(4-sec-butylpyridyl)imino) benzodipyrrole; 3,6,10,13,16,19-hexaazabicyclo[6.6.6] eicosane; and, 1,4,8,11-tetrakis-(2-pyridylmethyl)-1,4,8,11-tetraazacyclotetradecane); sulfur containing ligands (e.g., 1,4,7,10-tetrathiacyclotridecane and 1,4,8,11-tetrathiacyclotetradecane); and phosphorus containing ligands (e.g., α,α'-bis-(bis-(2-biphenylphosphino)ethyl) amino)ethane and α,α'-bis-(bis-(2-diphenylphosphino)m-xylene).

The invention also pertains to dimers and trimers of the ruthenium complexes described above. The coordination sphere of the metal center contain monodentate ligands (that are the same or different from each other) or it can contains a mixture of monodentate, bidentate and/or tridentate ligands. The oxidation state of each metal can be Ru(II)Ru (II); Ru(II)Ru(III); Ru(III)Ru(III); Ru(IV)Ru(IV); or Ru(III) Ru(IV). The counterions are the same as those described above.

Dimers will have the general formula:

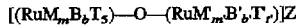

wherein the variables are described above and further wherein m and m' are independently 0, 1, 2, 3 or 5;
b and b' are independently 0, 1 or 2;
t and t' are independently 0 or 1; and
wherein m+b+t and m'+b'+t' are independently 2, 3, or 5.
Trimers will have the general formula:

wherein the variables are described above and further wherein m and m' are independently 0, 1, 2, 3 or 5;
m" is 0, 1, 2 or 4;
b, b' and b" are independently 0, 1 or 2;
t, t' and t" are independently 0 or 1; and
wherein m+b+t and m'+b'+t' are independently 2, 3 or 5 and wherein m"+b"+t" is 2, 3 or 4.

General procedures for making monomeric ruthenium complexes include: Vogt, Jr. et al., *Inorg. Chem.*, 4:1157 (1965); Ford et al., *J. Am. Chem. Soc.*, 90:1187 (1968); Marchant et al., *Inorg. Chem.*, 16:2160 (1977); Sullivan et al., *Inorg. Chem.*, 17:3334 (1978); Klassen et al., *Inorg. Chem.*, 19:1977 (1980); Klassen et al., *Inorg. Chem.*, 14:2733 (1975); Leising et al., *Inorg. Chem.*, 29:4569, (1990); Bessel et al., *J. Chem. Soc., Dalton trans.*, pp. 1563 (1993); Bernhard and Sargeson, *J. Chem. Soc. Chem. Commun.*, pp. 1516 (1985); Poon and Che, *J. Chem. Soc., Dalton trans.*, pp. 491 (1981); Walker and Taube, *Inorg. Chem.*, 20:2828 (1981); Mazzetto et al., *Polyhedron*, 12:971 (1993); Khan et al., *Inorg. Chim. Acta*, 189:165 (1991); Keppler et al., *Inorg. Chem.*, 26:844 (1987); and Kraus, *Inorg. Chim. Acta.*, 22:209 (1977). General procedures for making dimeric and trimeric ruthenium complexes include: Dopplet and Meyer, *Inorg. Chem.*, 26:2027 (1987); Geselowitz et al., *Inorg. Chem.*, 25:2015 (1986); Neubold et al., *Inorg. Chem.*, 28:459 (1989); Sasaki et al., *J. Am. Chem. Soc.*, 110:6251 (1988); Smith et al., *Inorg. Chem.*, 10:1943 (1971); Sudha et al., *J. Am. Chem. Soc.*, 32:3801 (1993); Weaver et al., *J. Am. Chem. Soc.*, 97:3039 (1975) and Emerson et al., *J. Am. Chem. Soc.*, 115:11799 (1993). See also U.S. patent application Ser. No. 08/331,388, filed Oct. 28, 1994 and U.S. patent application entitled "Novel Compounds for Inhibiting Immune Response", (Attorney's Docket Number PRO94-06A) filed concurrently herewith, the entire teachings of which are incorporated herein by reference.

It has now been discovered that the ruthenium complexes of this invention possess immunosuppressive activity as confirmed through a drug screen. Specific T cell proliferation was measured in response to antigen exposure in the presence or absence of ruthenium complexes. It was found that ruthenium complexes inhibited T cell proliferation by 50% ($IC_{50}$) at a concentration of about 1 to 100 nM. This compares favorably with cyclosporin A, which has an $IC_{50}$ at 15 nM (Table).

Ruthenium complexes can be administered orally, parenterally (e.g. intramuscularly, intravenously, subcutaneously), topically, nasally or via slow releasing microcarriers in dosage formulations containing a physiologically acceptable vehicle and optional adjuvants and preservatives. Suitable physiologically acceptable vehicles include saline, sterile water, creams, ointments or solutions.

Ruthenium complexes can be applied topically as a cream or ointment to locally deliver immunosuppressive concentrations of the drug without significant systemic exposure. Topical application may be the ideal way to deliver the compound in psoriasis and perhaps other inflammatory skin diseases such as contact dermatitis and pemphigusvulgaris.

The specific dosage level of active ingredient will depend upon a number of factors, including biological activity of the ruthenium complexes, age, body weight, sex, general health, severity of the particular disease to be treated and the degree of immune suppression desired, as well as appropriate pharmacokinetic properties. It should be understood that ruthenium complexes can be administered to mammals other than humans for immunosuppression of mammalian autoimmune diseases.

Ruthenium complexes can be administered in combination with other drugs to boost the immunosuppressive effect. Compounds that can be coadministered include steroids (e.g. methyl prednisolone acetate), NSAIDS and other known immunosuppressants such as azathioprine, 15-deoxyspergualin, cyclosporin, mizoribine, mycophenolate mofetil, brequinar sodium, leflunomide, FK-506, rapamcyin and related molecules. Dosages of these drugs will also vary depending upon the condition and individual to be treated.

The assay used to measure T cell growth inhibition was a human peripheral blood lymphocyte (PBL) proliferation assay using standard procedures known in the art. PBL's were chosen due to their known ability to proliferate in the presence of antigens derived from herpes simplex virus (HSV), Rubella or tetanus toxoid (TT). PBL growth inhibition was measured in terms of ruthenium complexes's ability to interfere with antigen induced lymphocyte proliferation.

Ruthenium complexes can be used to produce antibodies (e.g., polyclonal and monoclonal) against the complexes. Methods for making antibodies are well known. The antibodies can be used as a diagnostic tool for monitoring the amount of ruthenium complex in patient blood levels. The ability to closely monitor the amount of ruthenium complex provides a suitable means for controlling drug delivery to patients in both preclinical and clinical settings.

It has also been demonstrated that the ruthenium complexes have antiproliferative properties and in particular can inhibit cardiac smooth muscle cells. Based upon this, the ruthenium complexes can be used for the treatment of hyperproliferative vascular disorders, such as restenosis and atherosclerosis.

The invention will be further illustrated by the following non-limiting Exemplification:

EXEMPLIFICATION

PBL Antigen Specific Proliferation Assay

The lymphocytes were prepared by first separating them from the blood samples of several donors by Ficoll gradient separation as described by standard procedure known in the art. The isolated lymphocytes were then grown in RPMI 1640 medium containing 5% human AB serum, glutamine (2mM), penicillin/streptomycin, 100 U/ml/100 µg/ml sodium pyruvate (1 mM) and HEPES buffer (10 mM).

For assay purposes, PBL's were incubated at a density of $10^5$ per 200 µl of medium per well of a 96-well plate.

Tetanus toxoid (TT; Connaught Labs, Willow Dale, ON) was used as a stimulating antigen at a concentration of 5 LF/ml.

The test wells containing PBL's, were exposed to antigen, along with various dilutions of the ruthenium complexes solutions, as shown in the Table.

Subsequently, TT antigen/ruthenium complexes exposed PBL's were pulsed with 1 µCi/well of $^3$H-thymidine on day 5 using a standard procedure known in the art. The cells were then harvested 16 hours later onto a glass fiber filter using a TOMTEC cell harvester. Thymidine incorporation was measured by liquid scintillation counting using a Beta plate counter (Pharmacia, Inc., Piscataway, N.J.).

The results of the assay are shown in the Table.

TABLE

| Compound # | Structure | $IC_{50}$ (µg/mL) |
|---|---|---|
| PIC 060 | $[Ru_3O_2(NH_3)_{14}]Cl_6$ | 0.03 |
| PRO 1305 | $[Ru_3O_2(en)_2(NH_3)_{10}]Cl_6$ | 0.06 |
| PIC 1097 | $[Ru_2(\mu\text{-}O)(NH_3)_8Cl_2]Cl_3$ | 0.13 |
| PIC 1099 | $[Ru_2(\mu\text{-}O)(NH_3)_8(HCO_2)_2]Cl_3$ | 0.10 |
| PIC 1101 | $[Ru_2(\mu\text{-}O)(NH_3)_8(H_2O)_2](ClO_4)_5$ | 0.12 |
| PRO 1261 | $[Ru_2O(OAc)_2(py)_6](PF_6)_2$ | >100 |

TABLE-continued

| Compound # | Structure | IC$_{50}$ (μg/mL) |
|---|---|---|
| PRO 1306 | [Ru$_2$O(OAc)$_2$(Bipy)$_2$(py)$_2$](PF$_6$)$_2$ | >100 |
| PIC 1497 | [Ru$_2$O(Bipy)$_4$(H$_2$O)$_2$](ClO$_4$)$_4$ | 4.5 |
| PIC 1095 | [RuCl(NH$_3$)$_5$]Cl$_2$ | 15 |
| PIC 1096 | [Ru(NH$_3$)$_5$(4-MeIm)]Cl$_3$ | 0.45 |
| PIC 1098 | cis-[RuCl$_2$(NH$_3$)$_4$]Cl | >10 |
| PIC 1100 | trans-[Ru(SO$_4$)(py)(NH$_3$)$_4$]Cl | >10 |
| PRO 1422 | cis-Ru(DMSO)$_4$Cl$_2$ | >100 |
| PRO 1423 | [Ru(1-MeIm)$_6$]Cl$_2$ | 0.052 |
| PRO 1424 | [Ru(1-MeIm)$_6$](PF$_6$)$_3$ | 0.19 |
| PRO 1492 | [Ru(1-MeIm)$_6$]Cl$_3$ | 0.12 |
| PIC 1548 | trans-[Ru(Im)(py)(NH$_3$)$_4$]Cl$_3$ | 0.001 |
| PIC 1549 | cis-[Ru(Im)$_2$(NH$_3$)$_4$]Cl$_3$ | 0.0048 |
| PIC 1550 | trans-[Ru(Im)$_2$(NH$_3$)$_4$]Cl$_3$ | 0.0033 |
| PIC 1551 | trans-[Ru(Im)Cl(NH$_3$)$_4$]Cl$_2$ | >50 |
| PIC 1552 | ImH[trans-Ru(Im)$_2$Cl$_4$] | 35 |
| PIC 1553 | trans-[RuCl$_2$(cyclam)]Cl | >10 |
| PIC 1554 | trans-[Ru(SO$_4$)(Im)(NH$_3$)$_4$]Cl | 30 |
| PIC 1555 | K$_2$[Ru(H$_2$O)Cl$_5$] | 40 |
| PRO 1556 | [Ru(Im)$_6$]Cl$_2$ | 0.0067 |
| PRO 1696 | trans-[Ru(1-MeIm)$_4$Cl$_2$]Cl | 22 |
| PIC 1746 | 2-MeImH[trans-Ru(2-MeIm)$_2$Cl$_4$] | >50 |
| PIC 1747 | 4-MeImH[trans-Ru(2-MeIm)$_2$Cl$_4$] | 35 |
| PRO 1949 | [Ru(4-MeIm)$_6$]Cl$_2$ | 0.09 |
| PRO 1952 | [Ru(Im)$_6$]Cl$_3$ | 0.005 |
| PRO 1986 | [Ru(NH$_3$)$_5$(BzIm)]Cl$_3$ | 0.12 |
| PRO 1987 | [Ru(NH$_3$)$_5$(Im)]Cl$_3$ | 0.12 |
| PRO 1988 | [Ru(NH$_3$)$_5$(py)](PF$_6$)$_2$ | 0.017 |
| PRO 2032 | [Ru(NH$_3$)$_5$(py)]Cl(RuCl$_4$) | 0.0012 |
| PIC 2447 | [Ru(NH$_3$)$_6$]Cl$_3$ | 0.032 |
| PRO 2449 | [Ru(NH$_3$)$_5$(L-his)]Cl$_3$ | 0.014 |
| PRO 2450 | [Ru(NH$_3$)$_5$(4-MeIm-5-CHO)]Cl$_3$ | 0.35 |
| PRO 2453 | trans-[Ru(NH$_3$)$_4$(py)$_2$](PF$_6$)$_2$ | 0.005 |
| PRO 2503 | trans-[Ru(NH$_3$)$_4$(py)$_2$]Cl$_3$ | 0.026 |
| PRO 2841 | cis-[Ru(NH$_3$)$_4$(L-his)$_2$]Cl$_3$ | 0.027 |
| PRO 2842 | cis-[Ru(NH$_3$)$_4$(py)$_2$]Cl$_3$ | 0.004 |
| PRO 2843 | cis-[Ru(NH$_3$)$_4$(PPh$_3$)$_2$]Cl$_3$ | 0.57 |
| PRO 2844 | [Ru(NH$_3$)$_5$(4-pic)]Cl(RuCl$_4$) | 0.0006 |
| PRO 2844B | [Ru(NH$_3$)$_5$(4-pic)]Cl$_3$ | 0.0012 |
| PRO 2846 | cis-[Ru(NH$_3$)$_4$(1-MeIm)$_2$]Cl$_3$ | 0.004 |
| PRO 3006 | [Ru(en)$_3$]Cl$_3$ | 0.13 |
| PRO 3428 | [Ru(NH$_3$)$_5$(2-NH$_2$-5-Me-py)]Cl$_3$ | 0.04 |
| PRO 3429 | [Ru(NH$_3$)$_5$(4-NH$_2$-py)]Cl$_3$ | 0.0016 |
| PRO 4322 | cis-[Ru(NH$_3$)$_4$(4-pic)$_2$]Cl$_3$ | 0.012 |
| PRO 4325 | [Ru(NH$_3$)$_5$(PhCCH)]Cl$_2$ | 0.05 |
| PRO 4514 | [Ru(NH$_3$)$_5$(4-CH$_2$CO$_2$H-py)]Cl$_3$ | 0.0045 |
| PRO 4758 | [Ru(NH$_3$)$_5$(3-β-py-ala-OH)]Cl$_3$ | 0.015 |
| PRO 5024 | [Ru(NH$_3$)$_3$(Im)$_3$]Cl$_3$ | 0.0011 |

Im = Imidazole
py = pyridine
bipy = 2,2'-bipyridine
his = histidine
phen = 1,10-phenanthroline
cyclam = 1,4,8,11-tetraazacyclotetradecane
MeIm = methylimidazole
Ph = phenyl
DMSO = dimethylsulfoxide
en = ethylenediamine
BzIm = benzimidazole
pic = picoline
ala = alanine
PPh = phenyl phosphine

Equivalents

Those skilled in the art will recognize, or be able to ascertain, using no more than routine experimentation many equivalents to the specific embodiments of the invention described herein. Such equivalents are intended to be encompassed by the following claims:

We claim:

1. A method of preventing or substantially reducing a T-lymphocyte mediated immune response associated with autoimmune disease in a mammal in need thereof comprising administering to a mammal, a ruthenium complex having the general formula:

$$[RuM_mB_bT_tP_p]Z$$

wherein Ru is ruthenium having an oxidation state of 2, 3 or 4;

wherein M is a monodentate ligand selected from the group consisting of nitrogen containing ligands, phosphorus containing ligands, sulfur containing ligands, oxygen containing ligands and halide;

wherein m is 0, 1, 2, 3, 4 or 6;

wherein b is 0, 1, 2 or 3;

wherein t is 0, 1 or 2;

wherein p is 0 or 1;

wherein m+b+t+p is 1, 2, 3, 4, 5 or 6;

wherein B is a bidentate ligand selected from the group consisting of aliphatic amines, heterocyclic aromatic amines, sulfur containing ligands, oxygen containing ligands and phosphorus containing ligands;

wherein T is a tridentate ligand selected from the group consisting of nitrogen containing ligands, sulfur containing ligands, oxygen containing ligands and phosphorus containing ligands;

wherein P is a polydentate ligand selected from the group consisting of nitrogen containing ligands, oxygen containing ligands, sulfur containing ligands and phosphorus containing ligands; and wherein when the complex is charged then Z is at least counterion of appropriate charge to render the overall charge of the complex neutral.

2. The method of claim 1 wherein M is a nitrogen containing ligand selected from the group consisting of imidazole, picoline, pyridine, ammonia, triazole, pyrazole, quinoline, pyrazine, pyridazine, pyrimidine, quinoxaline, quinazoline, isoquinazoline, piperidine and their derivatives obtained by substituting for one or more hydrogen atoms with one or more of the following moieties C1–C5 alkyl, C2–C5 alkenyl, hydroxy, nitro, amino, carboxyl, ester, di-C 1–C4 alkyl amine, phenyl, benzyl, imidazole and combinations thereof.

3. The method of claim 2 wherein the imidazole has the general formula:

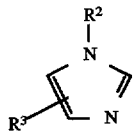

where R$^2$ and R$^3$ are independently selected from the group consisting of aryl, heteroaryl, linear and branched alkyl, —C(O)H, —COOR$^1$, —CONR$^1$, —COOH, —CH$_2$NH$_2$, —CH$_2$OSO$_2$, —CH$_2$COH, —CH$_2$COR$^1$, —CH$_2$CONR$^1$, —CH$_2$COOH, H, Cl, Br, I and NO$_2$; wherein R$^1$ is a linear or branched alkyl or aryl.

4. The method of claim 1 wherein B is selected from the group consisting of ethylene diamine, propylene diamine, 1,2-cyclohexane diamine and the corresponding alkylated amines thereof; 2,2'-bipyridine, 1,10-phenanthroline; 2-aminopicoline; potassium-bis-pyrazolyl borate, bis-pyrazolyl methane; and 1,2-bis(di-methylphosphino)ethane.

5. The method of claim 1 wherein B is represented by the general formula:

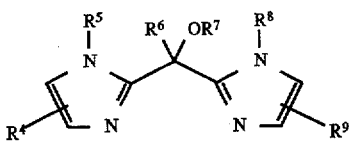

wherein $R^4$ to $R^9$ are the same or different from each other and are independently selected from the group consisting of aryl, heteroaryl, linear and branched alkyl, —C(O)H, —COOR$^1$, —CONR$^1$, —COOH, —CH$_2$NH$_2$, —CH$_2$OSO$_2$, —CH$_2$COH, —CH$_2$COR$^1$, —CH$_2$CONR$^1$, —CH$_2$COOH, H, Cl, Br, I and NO$_2$; wherein $R^1$ is a linear or branched alkyl or aryl.

6. The method of claim 1 wherein T is selected from the group consisting of 2,2',6'',2''-terpyridine, bis-(2-pyridylmethyl)amine; bis-(2-imidazolylmethyl)amine; potassium tris pyrazolyl borate; 1,4,7-triazacyclononane; and 1,4,7-trithiacyclononane.

7. The method of claim 1 wherein P is selected from the group consisting of 1,4,7,10-tetraazacyclododecane; 1,4,8,11-tetraazacyclotetradecane; 1,3,5,7-tetrakis-(2-(4-sec-butylpyridyl)imino)benzodipyrrole; 3,6,10,13,16,19-hexaazabicyclo[6.6.6]eicosane; 1,4,8,11-tetrakis-(2-pyridylmethyl)-1,4,8,11-tetraazacyclotetradecane); 1,4,7,10-tetrathiacyclotridecane and 1,4,8,11-tetrathiacyclotetradecane); α,α'-bis-(bis-(2-diphenylphosphino)ethyl)amino)ethane and α,α'-bis-(bis-(2-diphenylphosphino)m-xylene).

8. The method of claim 1 wherein Z is a counterion selected from the group consisting of F$^-$, Cl$^-$, Br$^-$, I$^-$, NO$_3^-$, NH$_4^+$, NR$^1_4{}^+$, PF$_6^-$, BPh$_4^-$, ClO$_4^-$, S$_8^{-2}$, S$_2$O$_7^{-2}$, RuCl$_4^{-2}$, K$^+$, SO$_4^{-2}$, Li$^+$, Na$^+$ and R$^1$ImH$^+$, where Im is imidazole; wherein $R^1$ is a linear or branched alkyl or aryl.

9. The method of claim 1, further comprising administering the ruthenium complex with asteroid and/or an immunosuppressant selected from the group consisting of cyclosporin, rapamycin, FK-506, azathioprine, mizoribine, mycophenolate mofetil, brequinar sodium, leflunomide and 15-deoxyspergualin.

10. The method of claim 1 wherein the complex selected from the group consisting of:

[RuCl(NH$_3$)$_5$]Cl$_3$;
[Ru(NH$_3$)$_5$(4-MeIm)]Cl$_3$;
cis-[RuCl$_2$(NM$_3$)4]Cl;
trans-[Ru(SO$_4$)(py)(NH$_3$)$_4$]Cl;
cis -Ru(DMSO)$_4$Cl$_2$;
[Ru(1-MeIm)$_6$]Cl$_2$;
[Ru(1-MeIm)$_6$](PF$_6$)$_3$;
[Ru(1-MeIm)$_6$]Cl$_3$;
trans-[Ru(Im)(py)(NH$_3$)$_4$]Cl$_3$;
cis-[Ru(Im)$_2$(NH$_3$)$_4$]Cl$_3$;
trans-[Ru(Im)$_2$(NM$_3$)$_4$]Cl$_3$;
trans-[Ru(Im)Cl(NH$_3$)$_4$]Cl$_2$;
ImH[trans-Ru(Im)$_2$Cl$_4$];
trans-[RuCl$_2$(cyclam)]Cl;
trans-[Ru(SO$_4$)(Im)(NH$_3$)$_4$]Cl;
K$_2$[Ru(H$_2$O)Cl$_5$];
[Ru(Im)$_6$]Cl$_2$;
trans-[Ru(1-MeIm)$_4$Cl$_2$]Cl;
2-MeImH[trans-Ru(2-MeIm)$_2$Cl$_4$];
4-MeImH[trans-Ru(4-MeIm)$_2$Cl$_4$];
[Ru(4 -MeIm)$_6$]Cl$_2$;
[Ru(Im)$_6$]Cl$_3$;
[Ru(NH$_3$)$_5$(BzIm)]Cl$_3$;
[Ru(NH$_3$)$_5$(Im)]Cl$_3$;
[Ru(NH$_3$)$_5$(py)](PF$_6$)$_2$;
[Ru(NH$_3$)$_5$(py)]Cl(RuCl$_4$);
[Ru(NH$_3$)$_6$]Cl$_3$;
[Ru(NH$_3$)$_5$(L-his)]Cl$_3$;
[Ru(NH$_3$)$_5$(4-MeIm-5-CHO)]Cl$_3$;
trans-[Ru(NH$_3$)$_4$(py)$_2$](PF$_6$)$_2$;
trans-[Ru(NH$_3$)$_4$(py)$_2$]Cl$_3$;
cis-[Ru(NH$_3$)$_4$(L-his)$_2$]Cl$_3$;
cis-[Ru(NH$_3$)$_4$(py)$_2$]Cl$_3$;
cis-[Ru(NH$_3$)$_4$(PPh$_3$)$_2$]Cl$_3$;
[Ru(NH$_3$)$_5$(4 -pic)]Cl (RuCl$_4$);
[Ru(NH$_3$)$_5$(4-pic)]Cl$_3$;
cis-[Ru(NH$_3$)$_4$(1-MeIm)$_2$]Cl$_3$;
[Ru(en)$_3$]Cl$_3$;
[Ru(NH$_3$)$_5$(2-NH$_2$-5-Me-py)]Cl$_3$;
[Ru(NH$_3$)$_5$(4 -NH$_2$-py)]Cl$_3$;
cis-[Ru(NH$_3$)$_4$(4-pic)$_2$]Cl$_3$;
[Ru(NH$_3$)$_5$(PhCCH)]Cl$_2$;
[Ru(NH$_3$)$_5$(4- CH$_2$CO$_2$H-py)]Cl$_3$;
[Ru(NH$_3$)$_5$(3-β-py-ala-OH)]Cl$_3$; and
[Ru(NH$_3$)$_3$(Im)$_3$]Cl$_3$;

wherein Im is imidazole, py is pyridine, his is histidine, DMSO is dimethylsulfoxide, bipy is 2,2'-bipyridine, BzIm is benzimidazole, pic is picoline, phen is 1,10-phenanthroline, ala is alanine, cyclam is 1,4,8,11-tetracyclotetradecane, MeIm is methylimidazole, Ph is phenyl, and PPh is phenyl phosphine.

11. The method of claim 10 wherein the autoimmune disease is selected from the group consisting of insulin dependent diabetes mellitus, rheumatoid arthritis, psoriasis, hyperplasia of the epidermis, contact dermatitis and symptoms associated therewith, steroid resistant asthma, multiple sclerosis and lupus erythematosus.

12. A method of preventing or substantially reducing a T-lymphocyte mediated immune response associated with autoimmune disease in a mammal, comprising administering to the mammal a ruthenium complex having the general formula:

$$[(RuM_mB_bT_t)-O-(RuM'_{m'}B'_{b'}T'_{t'})]Z$$

wherein Ru is ruthenium having an oxidation state of 2, 3 or 4;

wherein M and M' are independently a monodentate ligand selected from the group consisting of nitrogen containing ligands, phosphorus containing ligands, sulfur containing ligands and oxygen containing ligands and halide;

wherein m and m' are independently 0, 1, 2, 3 or 5;

wherein b and b' are independently 0, 1 or 2;

wherein t and t' are independently 0 or 1;

wherein m+b+t and m'+b'+t' are independently 2, 3 or 5;

wherein B and B' are independently a bidentate ligand selected from the group consisting of aliphatic amines, heterocyclic aromatic amines, sulfur containing ligands, oxygen containing ligands and phosphorus containing ligands;

wherein T and T' are independently a tridentate ligand selected from the group consisting of nitrogen containing ligands, sulfur containing ligands, oxygen containing ligands and phosphorus containing ligands; and wherein when the complex is charged then Z is at least one counterion of appropriate charge to render the overall charge of the complex neutral.

13. The method of claim 12 wherein M and M' are independently a nitrogen containing ligand selected from the group consisting of imidazole, pyridine, ammonia, triazole, pyrazole, quinoline, pyrazine, pyridazine, picoline, pyrimidine, quinoxaline, quinazoline, isoquinazoline, piperidine and their derivatives obtained by substituting for one or more hydrogen atoms with one or more of the following moieties C1–C5 alkyl, C2–C5 alkenyl, hydroxy, nitro, amino, carboxyl, ester, di-C1–C4 alkyl amine, phenyl, benzyl, imidazole and combinations thereof.

14. The method of claim 13 wherein the imidazole has the general formula:

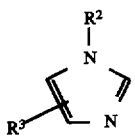

where $R^2$ and $R^3$ are independently selected from the groups consisting of aryl, heteroaryl, linear and branched alkyl, —C(O)H, —COOR$^1$, —CONR$^1$, —COOH, —CH$_2$NH$_2$, —CH$_2$OSO$_2$, —CH$_2$COH, —CH$_2$COR$^1$, —CH$_2$CONR$^1$, —CH$_2$COOH, H, Cl, Br, I and NO$_2$; wherein $R^1$ is a linear or branched alkyl or aryl.

15. The method of claim 12 wherein B and B' are independently selected from the group consisting of ethylene diamine, propylene diamine, 1,2-cyclohexane diamine and the corresponding alkylated amines thereof; 2,2'-bipyridine, 1,10-phenanthroline; 2-aminopicoline; potassium-bis-pyrazolyl borate, bis-pyrazolyl methane; and 1,2-bis(di-methylphosphino)ethane.

16. The method of claim 12 wherein B and B' are independently represented by the general formula:

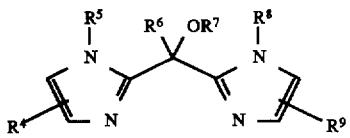

wherein $R^4$ to $R^9$ are the same or different from each other and are independently selected from the group consisting of aryl, heteroaryl, linear and branched alkyl, —C(O)H, —COOR$^1$, —CONR$^1$, —COOH, —CH$_2$NH$_2$, —CH$_2$OSO$_2$, —CH$_2$COH, —CH$_2$COR$^1$, —CH$_2$CONR$^1$, —CH$_2$COOH, H, Cl, Br, I and NO$_2$; wherein $R^1$ is a linear or branched alkyl or aryl.

17. The method of claim 12 wherein T and T' are independently selected from the group consisting of 2,2',6", 2"-terpyridine, bis-(2-pyridylmethyl)amine, bis-(2-imidazolylmethyl)amine; potassium tris pyrazolyl borate; 1,4,7-triazacyclononane; and 1,4,7-trithiacyclononane.

18. The method of claim 12 wherein Z is a counterion selected from the group consisting of F$^-$, Cl$^-$, Br$^-$, I$^-$, SO$_4^{-2}$, NO$_3^-$, NH$_4^+$, NR$^1{}_4^+$, PF$_6^-$, B$_4^-$, ClO$_4^-$, S$_8^{-2}$, S$_2$O$_7^{-2}$, RuCl$_4^{-2}$, K$^+$, Li$^+$, Na$^+$ and R$^1$ImH$^+$, where Im is imidazole; wherein $R^1$ is a linear or branched alkyl or aryl.

19. A method of preventing or substantially reducing a T-lymphocyte mediated immune response associated with autoimmune disease in a mammal in need thereof comprising administering to a mammal, a ruthenium complex having the general formula:

wherein Ru is ruthenium having an oxidation state of 2, 3 or 4;

wherein M, M' and M" are independently a mono-dentate ligand selected from the group consisting of nitrogen containing ligands, phosphorus containing ligands, sulfur containing ligands, oxygen containing ligands;

wherein m and m' are independently 0, 1, 2, 3 or 5;

wherein m" is 0, 1, 2 or 4;

wherein b, b' and b" are independently 0, 1 or 2;

wherein t, t' and t" are independently 0 or 1;

wherein m+b+t and m'+b'+t' are independently 2, 3 or 5 and wherein m"+b"+t"is 2, 3 or 4;

wherein B, B' and B" are independently a bidentate ligand selected from the group consisting of aliphatic amines, heterocyclic aromatic amines, sulfur containing ligands, oxygen containing ligands and phosphorus containing ligands;

wherein T, T' and T" are independently a tridentate ligand selected from the group consisting of nitrogen containing ligands, sulfur containing ligands, oxygen containing ligands and phosphorus containing ligands; and wherein when the complex is charged then Z is at least one counterion of appropriate charge to render the overall charge of the complex neutral.

20. The method of claim 19 wherein M, M' and M" are independently a nitrogen containing ligand selected from the group consisting of imidazole, picoline, pyridine, ammonia, triazole, pyrazole, quinoline, pyrazine, pyridazine, pyrimidine, quinoxaline, quinazoline, isoquinazoline, piperidine and their derivatives obtained by substituting for one or more hydrogen atoms with one or more of the following moieties C1–C5 alkyl, C2–C5 alkenyl, hydroxy, nitro, amino, carboxyl, ester, di-C1–C4 alkyl amine, phenyl, benzyl, imidazole and combinations thereof.

21. The method of claim 20 wherein the imidazole has the general formula:

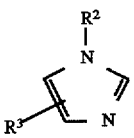

where $R^2$ and $R^3$ are independently selected from the group consisting of aryl, heteroaryl, linear and branched alkyl, —C(O)H, —COOR$^1$, —CONR$^1$, —COOH, —CH$_2$NH$_2$, —CH$_2$OSO$_2$, —CH$_2$COH, —CH$_2$COR$^1$, —CH$_2$CONR$^1$, —CH$_2$COOH, H, Cl, Br, I and NO$_2$; wherein $R^1$ is a linear or branched alkyl or aryl.

22. The method of claim 20 wherein B, B' and B" are independently selected from the group consisting of ethylene diamine, propylene diamine, 1,2-cyclohexane diamine and the corresponding alkylated amines thereof; 2,2'-bipyridine, 1,10-phenanthroline; 2-aminopicoline; potassium-bis-pyrazolyl borate, bis-pyrazolyl methane; and 1,2-bis(di-methyl-phosphino)ethane.

23. The method of claim 20 wherein B, B' and B" are independently represented by the general formula:

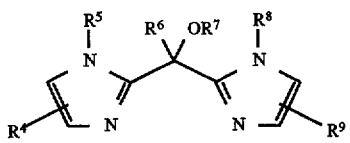

wherein $R^4$ to $R^9$ are the same or different from each other and are independently selected from the group consisting of aryl, heteroaryl, linear and branched alkyl, —C(O)H, —COOR$^1$, —CONR$^1$, —COOH, —CH$_2$NH$_2$, —CH$_2$OSO$_2$, —CH$_2$COH, —CH$_2$COR$^1$, —CH$_2$CONR$^1$, —CH$_2$COOH, H, Cl, Br, I and NO$_2$; wherein $R^1$ is a linear or branched alkyl or aryl.

24. The method of claim 20 wherein T, T' and T" are selected from the group consisting of 2,2',6",2"'-terpyridine, bis-(2-pyridyl)methylamine; bis-(2-imidazolylmethyl)amine; potassium tris pyrazolyl borate; 1,4,7-triazacyclononane; and 1,4,7-trithiacyclononane.

25. The method of claim 19 wherein Z is a counterion selected from the group consisting of F$^-$, Cl$^-$, Br$^-$, I$^-$, SO$_4^{-2}$, NO$_3^-$, NH$_4^+$, NR$^1{}_4^+$, PF$_6^-$, BPh$_4^-$, ClO$_4^-$, S$_8^{-2}$, S$_2$O$_7^{-2}$, RuCl$_4^{-2}$, K$^+$, Li$^+$, Na$^+$ and R$^1$ImH$^+$, where Im is imidazole; wherein $R^1$ is a linear or branched alkyl or aryl.

26. A method for treating hyperproliferative vascular disorders comprising administering a ruthenium complex having the general formula:

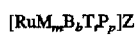

wherein Ru is ruthenium having an oxidation state of 2, 3 or 4;

wherein M is a monodentate ligand selected from the group consisting of nitrogen containing ligands, phosphorus containing ligands, sulfur containing ligands, oxygen containing ligands and halide;

wherein m is 0, 1, 2, 3, 4 or 6;

wherein b is 0, 1, 2 or 3;

wherein t is 0, 1 or 2;

wherein p is 0 or 1;

wherein m+b+t+p is 1, 2, 3, 4, 5 or 6;

wherein B is a bidentate ligand selected from the group consisting of aliphatic amines, heterocyclic aromatic amines, sulfur containing ligands, oxygen containing ligands and phosphorus containing ligands;

wherein T is a tridentate ligand selected from the group consisting of nitrogen containing ligands, sulfur containing ligands, oxygen containing ligands and phosphorus containing ligands;

wherein P is a polydentate ligand selected from the group consisting of nitrogen containing ligands, oxygen containing ligands, sulfur containing ligands and phosphorus containing ligands; and wherein when the complex is charged then Z is at least one counterion of appropriate charge to render the overall charge of the complex neutral.

27. A method of preventing or substantially reducing a T-lymphocyte mediated immune response associated with graft rejection in a mammal in need thereof comprising administering to a mammal, a ruthenium complex having the general formula:

[RuM$_m$B$_b$T$_t$P$_p$]Z wherein Ru is ruthenium having an oxidation state of 2, 3 or 4;

wherein M is a monodentate ligand selected from the group consisting of nitrogen containing ligands, phosphorus containing ligands, sulfur containing ligands, oxygen containing ligands and halide;

wherein m is 0, 1, 2, 3, 4 or 6;

wherein b is 0, 1, 2 or 3;

wherein t is 0, 1 or 2;

wherein p is 0 or 1;

wherein m+b+t+p is 1, 2, 3, 4, 5 or 6;

wherein B is a bidentate ligand selected from the group consisting of aliphatic amines, heterocyclic aromatic amines, sulfur containing ligands, oxygen containing ligands and phosphorus containing ligands;

wherein T is a tridentate ligand selected from the group consisting of nitrogen containing ligands, sulfur containing ligands, oxygen containing ligands and phosphorus containing ligands;

wherein P is a polydentate ligand selected from the group consisting of nitrogen containing ligands, oxygen containing ligands, sulfur containing ligands and phosphorus containing ligands; and wherein when the complex is charged then Z is at least one counterion of appropriate charge to render the overall charge of the complex neutral.

28. A method of preventing or substantially reducing a T-lymphocyte mediated immune response associated with graft rejection in a mammal comprising administering to a mammal, a ruthenium complex having the general formula:

[Ru(Im)$_6$]Cl$_2$ wherein Im is imidazole.

* * * * *

UNITED STATES PATENT AND TRADEMARK OFFICE
CERTIFICATE OF CORRECTION

PATENT NO. : 5,708,022
DATED : January 13, 1998
INVENTOR(S) : Cecilia M. Bastos and Timothy D. Ocain It is certified that error appears in the above-identified patent and that said Letters Patent is hereby corrected as shown below:

Claim 9, Col. 9, line 2, delete "asteroid" and insert ---a steroid---.

Claim 10, Col. 9 line 46, delete "cis-[RUCl$_2$(NM$_3$)4]Cl;" and insert ---cis-[RuCl$_2$(NH$_3$)4]Cl;---.

Claim 18, Col. 11, lines 62 and 63, after "PF$_6^-$", delete "B$_4^-$" and add ---BPh$_4$,---.

Claim 22, Col. 12, line 59, delete "20" and insert ---19---.

Claim 23, Col. 12, line 66, delete "20" and insert ---19---.

Claim 24, Col. 13, line 15, delete "20" and insert ---19---.

Signed and Sealed this

Nineteenth Day of May, 1998

Attest:

BRUCE LEHMAN

*Attesting Officer*  *Commissioner of Patents and Trademarks*